United States Patent [19]

Frayman et al.

[11] Patent Number: 5,279,541
[45] Date of Patent: Jan. 18, 1994

[54] TAMPON APPLICATOR

[75] Inventors: Max Frayman, Longmeadow; Richard J. Lindsay, North Brookfield, both of Mass.; E. Russell Sprague, Palm City, Fla.

[73] Assignee: Tambrands Inc., White Plains, N.Y.

[21] Appl. No.: 973,072

[22] Filed: Nov. 6, 1992

[51] Int. Cl.⁵ .................................. A61F 13/20
[52] U.S. Cl. ................................ 604/14; 604/11; 604/13; 604/15; 604/904
[58] Field of Search ............................ 604/11-

[56] References Cited

U.S. PATENT DOCUMENTS 3,204,635  9/1965  Voss et al.
3,347,234 10/1967  Voss.
4,508,531  4/1985  Whitehead.

FOREIGN PATENT DOCUMENTS 2114448A  8/1983  United Kingdom.
2132484A  7/1984  United Kingdom.
2133695   8/1984  United Kingdom ........... 604/358
2142906   1/1985  United Kingdom.

Primary Examiner—Randall L. Green
Assistant Examiner—A. Zuttarelli
Attorney, Agent, or Firm—Fish & Richardson

[57] ABSTRACT

An improved tampon applicator for insertion of a tampon into a body cavity is provided, including a paper tampon holder tube having an expulsion end dimensioned for insertion into the body cavity and including a plurality of contiguous segments separated by slits, and a plunger, telescopically and slidably mounted in the holder distal to the expulsion end and adapted to expel the tampon from the holder when pushed manually into the holder. As the tampon is expelled, the segments bend open at a hinge region. The segments of the improved applicator bend outwardly during expulsion with significantly reduced applied force, improving user comfort. In one aspect, the tampon holder includes a plurality of small cuts extending circumferentially from the slits through the paper in the vicinity of the hinge region. The cuts reduce the width of the petal segments, and thereby reduce the bending moment and rigidity at the hinge region.

12 Claims, 3 Drawing Sheets

TAMPON APPLICATOR

BACKGROUND OF THE INVENTION

This invention relates to a tampon applicator, formed from a paper laminate.

Tampon applicators comprising a pair of telescopically arranged tubes have long been known in the art. Typically, these applicators comprise a tampon holder tube and a plunger tube, telescopically disposed such that a portion of the plunger tube is within the holder tube.

Some applicators have the tampon exposed at the end intended for vaginal insertion (the expulsion end), while others provide a rounded expulsion end, with the tampon covered by a plurality of segments, referred to in the art as "petals", which open during tampon expulsion. A tampon having the latter construction is disclosed in U.S. Pat. No. 5,087,239, the disclosure of which is incorporated herein by reference. In this applicator, a weakened region, e.g., a groove, is provided at the base of the segments.

However, the force required to bend the segments during expulsion may be undesirably high, even if a groove is provided at the base of the segments. The high force required may cause discomfort to the user, or may prevent the tampon from being properly expelled.

SUMMARY OF THE INVENTION

The invention features an improved tampon applicator for insertion of a tampon into a body cavity, including a paper tampon holder tube having an expulsion end dimensioned for insertion into the body cavity and including a plurality of contiguous petal segments separated by slits, and a plunger, telescopically and slidably mounted in the holder distal to the expulsion end and adapted to expel the tampon from the holder when pushed manually into the holder. As the tampon is expelled, the segments bend open at a hinge region. The segments of the improved applicator bend outwardly during expulsion with significantly reduced applied force, improving user comfort.

The tampon holder includes a plurality of small cuts extending circumferentially from the petal slits in the vicinity of the hinge region. The cuts may take a variety of forms, so long as they narrow the circumferential extent, i.e., the width, of the petal segments. The cuts reduce the bending moment and rigidity at the hinge region, both by shortening the width of the "beam" being bent, and by reducing the curvature of the "beam". In preferred embodiments, the tampon holder is a paper laminate; there is a cut at or near the base of each petal slit; the cuts have a length that effectively narrows the width of the petal segments by anywhere from about 15 to 50 percent.

Other features and advantages of the invention will be apparent from the following description of preferred embodiments, and from the claims.

DESCRIPTION OF THE PREFERRED EMBODIMENTS

Figure 1:
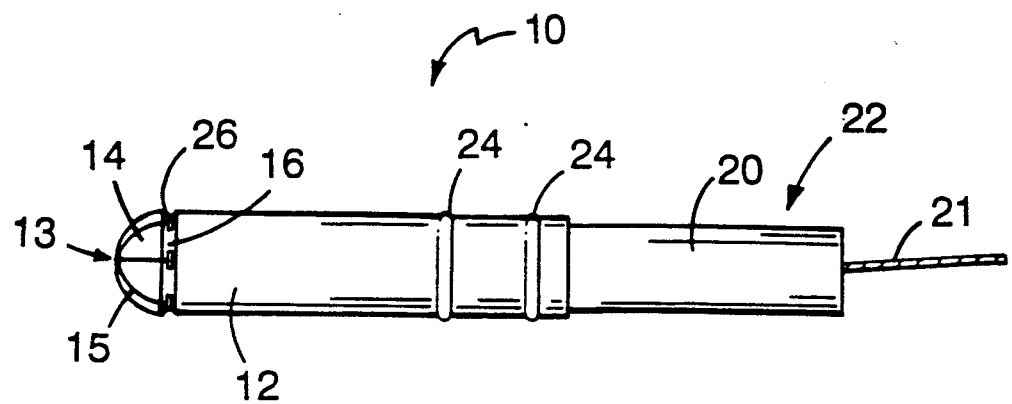
FIG. 1 shows a tampon applicator according to one embodiment of the invention.
Figure 2:
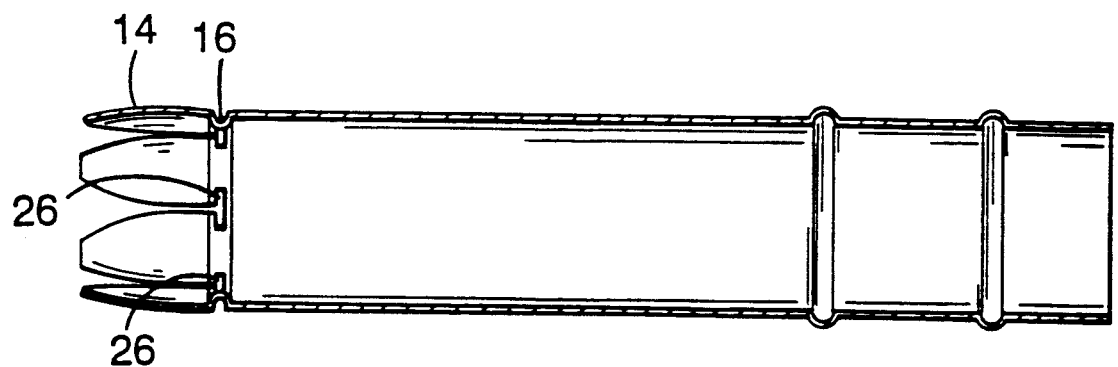
FIG. 2 shows a partial side cross-sectional view of the applicator of FIG. 1, enlarged to show detail.
Figure 2A:
FIG. 2a shows a front view of the triangular notches which are removed from the tampon expulsion end to form the petal segments.

An applicator 10 according to a preferred embodiment of the invention is shown in FIGS. 1 and 2. The applicator comprises tubular tampon holder 12, and plunger 20, telescopically and slidably mounted inside of tampon holder 12. A tampon 13 is retained within tampon holder 12, and its expulsion end is surrounded by contiguous petal segments 14, separated by petal slits 15. Petal segments 14 are formed by cutting out triangular notches of the paper laminate (as is known, e.g., in U.S. Pat. No. 5,087,239). This may occur either prior to formation of the tube by stamping, in convolutely wound tampons, or after formation of a spirally wound tube. The segments are then heat-formed into a dome-shape.

In use, as plunger 20 is pressed inwardly, petal segments 14 bend open at a hinge region, and the tampon is expelled through the expulsion end.

To reduce the expulsion force required to bend the petal segments open at the hinge region, a weakened region in the form of a groove 16 is embossed into the outer surface of tampon holder 12 in the vicinity of the hinge region. Groove 16 extends circumferentially around, at, or near, the base of the segments. The weakened region may take a variety of forms other than a groove (e.g., it may be a slot or perforation, and it may be continuous or discontinuous). Tampon withdrawal cord 21 extends out of distal end 22 of the applicator. Rings 24 are embossed into tampon holder 12 at its distal end, to provide a gripping surface for the user.

Substantial further reduction in expulsion force is achieved by providing a plurality of small circumferential cuts 26 at the vicinity of the hinge region. Each cut extends circumferentially a small distance in each direction from the slit 15. The cuts reduce the bending moment and rigidity at the hinge region, both by shortening the width of the "beam" being bent, and by reducing the curvature of the "beam". In a preferred embodiment, each cut is from about 0.04 to 0.09" long, about 0.01 to 0.03" high, and has a width approximately equal to that of slits 15.

The tampon holder and plunger is preferably constructed from a paper laminate, e.g., as described in pending U.S. application Ser. No. 07/819,753.

Any conventional process can be used to form the tubes, e.g., spiral or convolute winding of the individual layers, each layer on top of the previous layer about a common central axis. Spiral winding is generally preferred. It is also preferred that the seams formed in each layer during spiral winding be offset from the seams in other layers. These methods are well known to those skilled in the art.

The circumferential cuts may be used in a tampon applicator such as disclosed in the commonly-assigned application of Tomaszewski et al., Ser. No. 07/973,156, filed on even date herewith (incorporated herein by reference).

Figure 3:
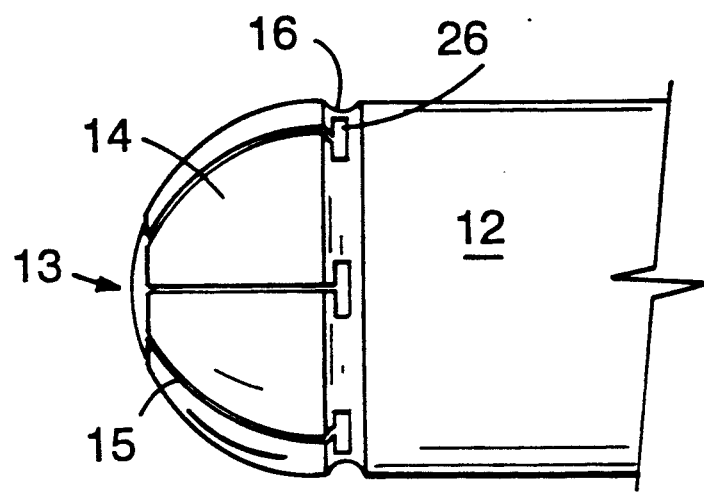
FIG. 3 is an enlarged view of the expulsion end of the embodiment shown in FIG. 1.
Figure 3A:
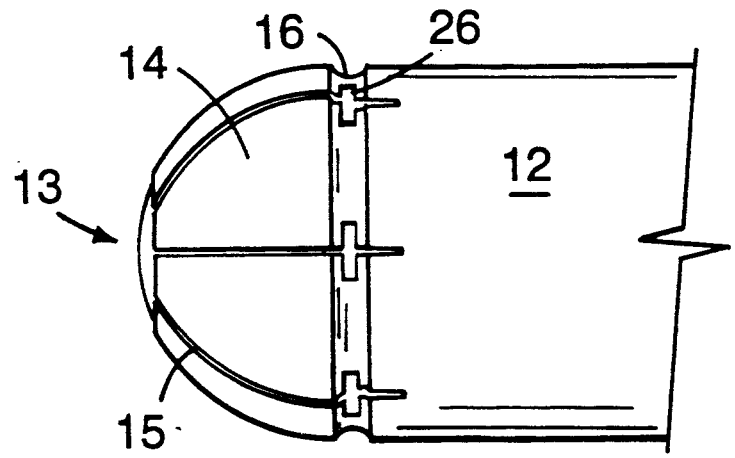
FIGS. 3a-3e show the expulsion ends of tampon applicators according to some of many alternate embodiments of the invention.
Figure 3B:
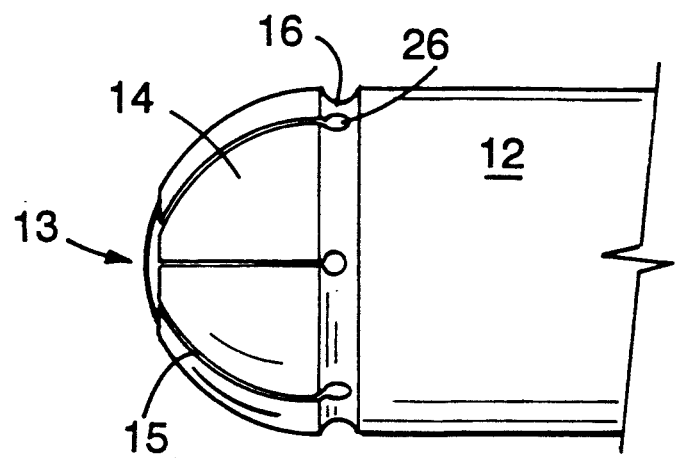
Figure 3C:
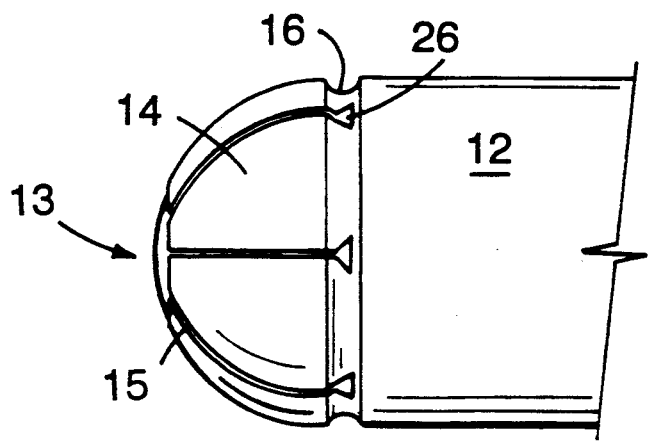
Figure 3D:
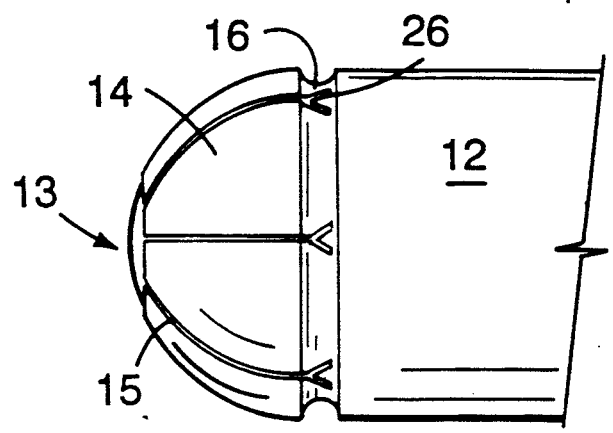
Figure 3E:
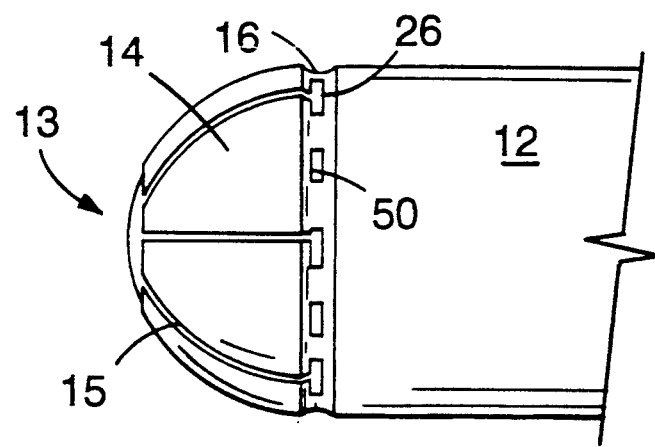

While preferred embodiments have been described above, other variations and modifications are within the scope of the following claims. The slits separating the petal segments can extend beyond the hinge region (e.g., as shown in FIG. 3a). The circumferential cuts need not extend exactly circumferentially, but could be cut at an angle to the circumferential direction (as shown in FIG. 3d); and other shapes such as circular and triangular cut outs (as shown in FIGS. 3b and 3c) could be used, as long as they have some circumferential extent. The cuts need not actually remove material, as shown, but could simply be slits in the paper. The cuts need not be centered on the slits (as shown in FIGS. 3 and 3a), but could be offset (as shown in FIG. 3e), and the alignment with slits could vary randomly from slit to slit (FIG. 3e). Additional cuts could be positioned intermediate the slits (as at 50 in FIG. 3e). Although a laminated paper construction has been disclosed, the invention could be applied to nonlaminated paper constructions, and to plastic applicators.

We claim:

1. A tampon applicator for insertion of a tampon into a body cavity, comprising
    a tampon holder tube having an expulsion end dimensioned for insertion into the body cavity, said tampon holder tube including
        a plurality of segments each having a width and thickness and being separated from other at the expulsion end by slits,
        and a hinge region adjacent each said segment in which each said segments bends open during expulsion at the hinge region;
    a plunger, telescopically and slidably mounted in said holder distal to said expulsion end and adapted to expel said tampon from said tampon holder tube when pushed manually into said tampon holder tube;
    said tampon holder tube including a plurality of cuts, each cut being located in said hinge region and extending entirely through said thickness of a said segment, and circumferentially from a said slit a distance sufficient to narrow said width of said segment.

2. The applicator of claim 1 wherein said tampon holder tube comprises at least one layer of paper.

3. The applicator of claim 2 wherein the expulsion end of said tampon holder tube further comprises a circumferentially-extending weakened region in the hinge region.

4. The applicator of claim 3 wherein said weakened region comprises a circumferential groove.

5. The applicator of claim 3 wherein said weakened region comprises a circumferential groove and said cuts extend in said circumferential groove.

6. The applicator of claim 3 wherein said weakened region comprises a plurality of cuts, at least one cut in the center of the base of each said segment.

7. The applicator of claim 2 wherein said circumferential cuts extend from the ends of the slits separating the segments.

8. The applicator of claim 2 wherein at each slit there is only one circumferential cut, which extends circumferentially a small distance in one direction from said slit.

9. The applicator of claim 2 wherein at each slit there are two circumferential cuts, one extending circumferentially a small distance in each circumferential direction.

10. The applicator of claim 2 wherein said circumferential cuts include cuts having both a circumferential and a longitudinal extent.

11. The applicator of claim 2 wherein said circumferential cuts reduce said width of the segments from about 15 to 50 percent.

12. An applicator of claim 1, 2, or 3 wherein said tampon holder tube has a dome-shaped expulsion end.

* * * * *

UNITED STATES PATENT AND TRADEMARK OFFICE
CERTIFICATE OF CORRECTION

PATENT NO. : 5,279,541

DATED : 1/18/94

INVENTOR(S) : Max Frayman, Richard J. Lindsay, E. Russell Sprague

It is certified that error appears in the above-identified patent and that said Letters Patent is hereby corrected as shown below:

Column 3, lines 24-25, delete "at the expulsion end by slits" and insert --said segments by slits at the expulsion end--.

Column 3, line 27, "segments" should be --segment--.

Signed and Sealed this

Thirty-first Day of May, 1994

Attest:

BRUCE LEHMAN

*Attesting Officer*   Commissioner of Patents and Trademarks